United States Patent [19]

Patterson

[11] Patent Number: 4,889,432

[45] Date of Patent: Dec. 26, 1989

[54] DENTAL MIXER APPARATUS

[76] Inventor: Roosevelt Patterson, 816 Hillview Heights T-1, Nashville, Tenn. 37204

[21] Appl. No.: 307,308

[22] Filed: Feb. 7, 1989

[51] Int. Cl.$^4$ .................. B01F 13/06; B01F 15/02; B01F 7/22; B29B 7/16

[52] U.S. Cl. .................. 366/139; 222/388; 222/568; 366/177; 366/189; 366/194; 366/249; 366/289; 425/203

[58] Field of Search ............ 366/139, 150, 162, 167, 366/168, 172, 173, 177, 194, 184, 189, 204, 197, 207, 247, 249, 250, 251, 286, 289, 331, 602, 244, 245, 246, 248, 252, 253, 254; 222/229, 386, 388, 567, 568, 152; 425/200, 203; 433/25, 34, 36

[56] References Cited

U.S. PATENT DOCUMENTS

| | | | |
|---|---|---|---|
| 1,458,282 | 6/1923 | Fairbanks | 366/289 |
| 3,131,912 | 5/1964 | Steinbock, Jr. | 366/139 X |
| 3,468,520 | 9/1969 | Duryea et al. | 366/248 X |
| 3,557,411 | 1/1971 | Ravasi | 222/152 X |
| 3,640,510 | 2/1972 | Lea | 366/139 |
| 4,277,184 | 7/1981 | Solomon | 366/139 X |
| 4,577,973 | 3/1986 | Occelli | 366/139 |
| 4,668,561 | 5/1987 | Ney | 222/386 X |
| 4,721,390 | 1/1988 | Lidgren | 366/139 |
| 4,787,751 | 11/1988 | Bakels | 366/139 X |

Primary Examiner—Harvey C. Hornsby
Assistant Examiner—Scott J. Haugland
Attorney, Agent, or Firm—Harrington A. Lackey

[57] ABSTRACT

A dental mixer apparatus including an upright mixing chamber having an upper open end for receiving dental impression materials and a plunger member suspended coaxially upon an elongated rotary driven mixer shaft for vertical reciprocable movement between a lower operative position in which the plunger is received within the mixing chamber and an upper inoperative position above the mixing chamber. A rotary mixer head is driven by the mixer shaft below the mixing chamber for mixing the materials within the mixing chamber. A suction conduit is provided to suck air from the mixing chamber in order to minimize voids and bubbles within the mixed ingredients. The mixer shaft is supported by a support bracket which is pivotally mounted to permit the mixer shaft and plunger to swing away from their normal vertical position above the mixing chamber to provide more working space above the mixing chamber. Optionally, the mixing chamber may be supported in a receptacle hinged to a base member to permit swinging movement of the mixing chamber away from its position beneath the mixer head. The plunger may also be depressed to discharge the mixed ingredients from an opening in the bottom of the mixing chamber.

13 Claims, 3 Drawing Sheets

DENTAL MIXER APPARATUS

BACKGROUND OF THE INVENTION

This invention relates to a mixer apparatus, and more particularly to an apparatus for mixing and dispensing dental impression materials.

Conventionally, dental impression materials are usually mixed manually with implements, such as a mortar and pestle. Because the mixed ingredients set rapidly, the mixing and application of the impression materials must be conducted quickly. Because of the time constraints, sometimes the mixing is incomplete. Usually, two operators, the dentist and his assistant, are necessary for the mixing and dispensing of the impression materials to form a compound for filling tooth cavities.

Furthermore, other types of dental mixing apparatus are disclosed in the following U.S. patents:

| | | |
|---|---|---|
| 2,224,967 | Kaye | Dec. 17, 1940 |
| 3,603,564 | Price et al | Sep. 7, 1971 |
| 3,951,387 | Warden et al | Apr. 20, 1976 |
| 4,184,776 | Shampanier | Jan. 22, 1980 |

All of the above patents disclose various types of dental mixing apparatus including a container for the dental ingredients and a rotary blade for mixing the ingredients within the container.

All of the above patents, except Kaye, disclose rotary mixing blades which are power-driven, such as by an electrical motor.

All of the above patents, except Warden et al disclose a plunger member for forcing the mixed ingredients from one end of the container.

The above Kaye patent discloses a plunger 93 through which extends coaxially a rotary shaft 98 carrying the mixing blade or stirrer 96.

None of the above patents discloses a mixing chamber which is evacuated, much less, a mixer apparatus including a cylindrical plunger carrying a suction conduit for evacuating the mixing chamber when the plunger is received within the mixing chamber.

Furthermore, none of the above patents disclose a support bracket carrying a mixer shaft and plunger mounted for vertical adjustment above a mixing chamber and means for swinging the support bracket about a horizontal axis to working space above the mixing chamber.

SUMMARY OF THE INVENTION

The dental mixing apparatus made in accordance with this invention includes a mixing chamber for dental impression materials and a cooperating plunger and mixing head for mixing the ingredients and also for dispensing the mixed ingredients.

The dental mixing apparatus made in accordance with this invention is provided with support means for readily introducing the plunger and mixer head into the mixing chamber and also for removing the mixer head and plunger from the chamber to an inoperative position sufficiently elevated to permit charging and discharging of the mixing chamber.

Another object of this invention is to provide a dental mixer apparatus incorporating a plunger having a suction conduit adapted to remove air from the mixing chamber when the plunger is received within the mixing chamber, in order to minimize voids and bubbles within the mixed ingredients.

A further object of this invention is to provide in a dental mixing apparatus, a structure for introducing various types of dental impression materials into the mixing chamber through the use of charge syringes.

Another object of this invention is to provide a mixing chamber which may be quickly removed, charged or discharged and replaced or discarded, before or after the mixing procedure.

The dental mixer apparatus made in accordance with this invention incorporates a rotary driven mixer shaft carrying a mixer head supported above an upright mixing chamber, and a plunger carrying a suction conduit suspended upon the shaft above the mixer head in such a manner that the plunger and mixer head may be depressed into the mixing chamber for mixing the ingredients under sealed and evacuated conditions. Preferably, the mixer shaft is mounted upon a support bracket vertically and slidably received upon one or more upright guide posts and normally biased into an upper inoperative position to permit depression of the support bracket until the plunger and mixer head are telescopingly received within the open end of the mixing chamber in an operative position for evacuation and mixing of the ingredients within the mixing chamber.

BRIEF DESCRIPTION OF THE DRAWINGS

FIG. 8 is an enlarged fragmentary plan view taken along he line 8—8 of FIG. 1, with the motor shown in phantom.

DESCRIPTION OF THE PREFERRED EMBODIMENTS

Figure 1:
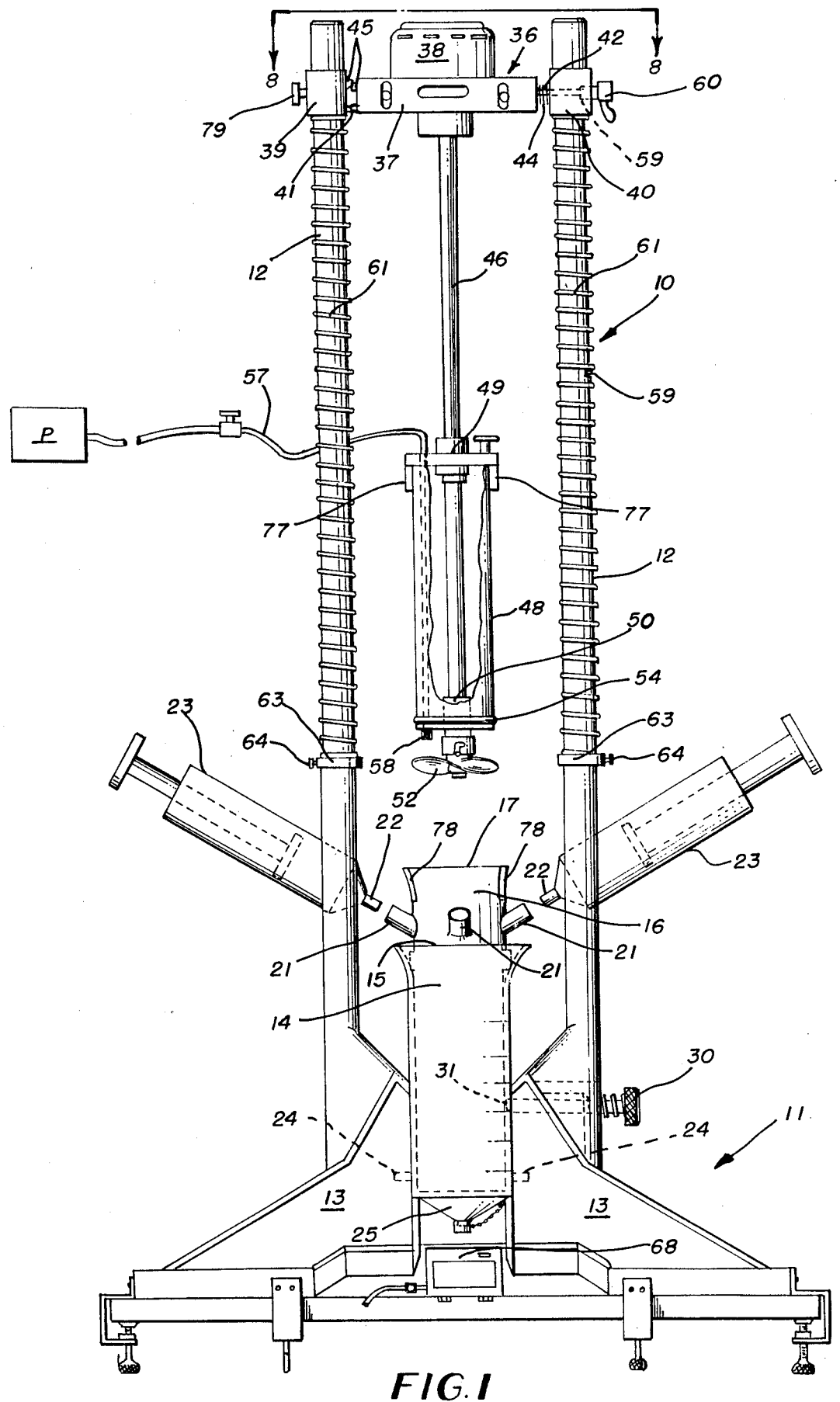
FIG. 1 is a front elevational view of the apparatus made in accordance with this invention, with the plunger and mixer head in their elevated, inoperative positions, and with a portion of the plunger broken away.
Figure 2:
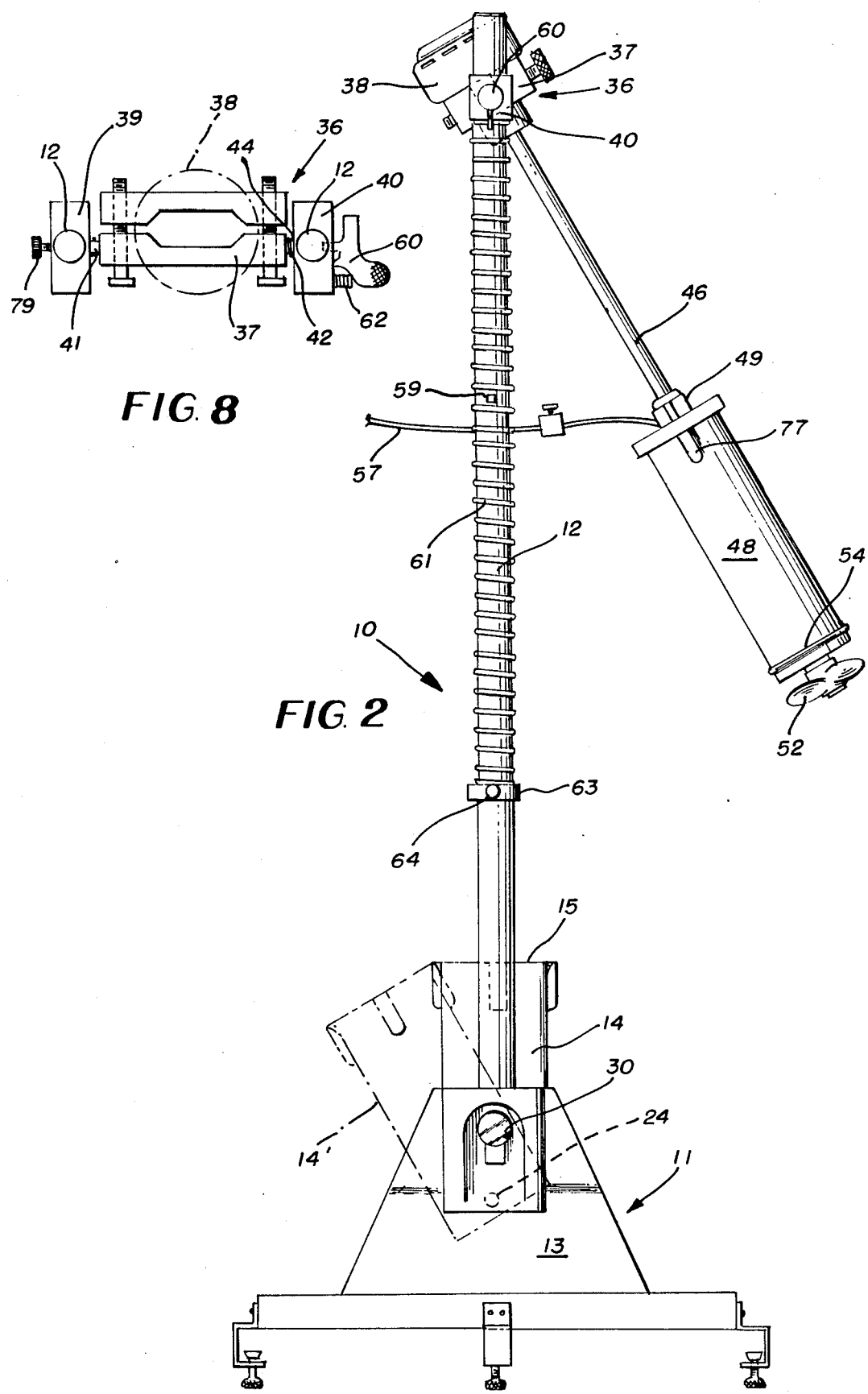
FIG. 2 is a right side elevational view of the apparatus disclosed in FIG. 1, with the mixer shaft and plunger swung to an out-of-the-way position, and with the mixing chamber receptacle shown in its operative position in solid lines and in a pivotal, inoperative position in phantom, with the mixing chamber removed.

Referring now to the drawings in more detail, FIGS. 1 and 2 disclose a dental mixer apparatus 10 made in accordance with this invention including a base 11, and one or more, such as the pair of, upright guide rods 12, fixed to and projecting upward from the base 11. The base 11 includes a air of base members 13 spaced apart to provide an opening or receiving an upright holder or tubular receptacle 14 having an open upper flared end or mouth 15. The receptacle 14 is adapted to receive a substantially cylindrical mixing chamber 16 also having an open upper end 17 spaced above the mouth 15 in operative position.

The receptacle 14 preferably has an open bottom to receive the bottom portion of the mixing chamber 16 and to permit free passage of any material discharged from the bottom portion of the mixing chamber 16.

Figure 3:
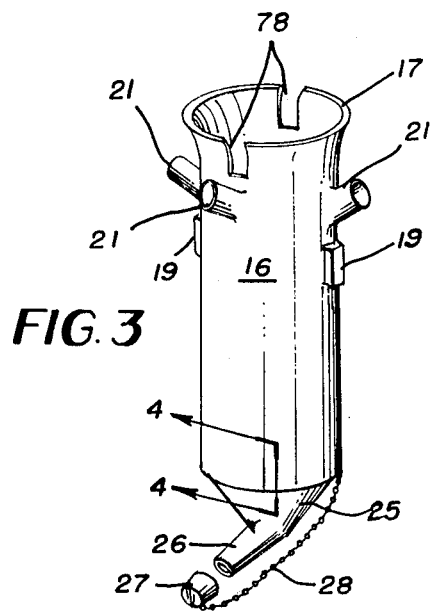
FIG. 3 is a top perspective view of the mixing chamber made in accordance with this invention.
Figure 6:
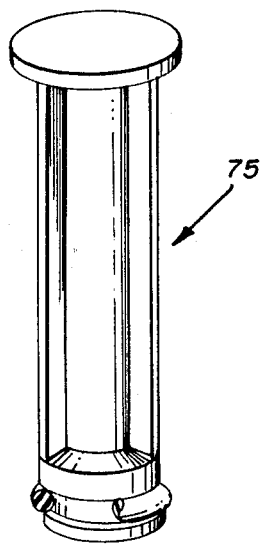
FIG. 6 is a top perspective view of a modified manually operated plunger, with a portion of the sealing O-ring broken away.

As disclosed in FIGS. 3 and 6, the cylindrical mixing chamber 16 is provided with a pair of radially projecting ears 19 or projections which are adapted to be received in corresponding slots 20 formed in the opposed inner walls of the receptacle 14. Thus, when the mixing chamber 16 is inserted into the receptacle 14, the mixing chamber 16 is fully supported by the cooperating ears 19 and slots 20.

The ears 19 and slots 20 are so related that the upper open end 17 of the mixing chamber 16 will be spaced above the mouth 15 of the receptacle 14 sufficiently to avoid interference with the inlet spouts 21 projecting radially from the upper wall portion of the mixing chamber 16. The inner diameters of the tubular inlet spouts 21 are large enough to receive the nozzles or discharge tips 22 of charge syringes 23. Each of the syringes 23 is adapted to be charged with the desired dental impression materials for discharge into the mixing chamber 16.

The receptacle 14 may be provided with diametrically opposed outwardly projecting hinge pins or pintles 24 which are journaled within corresponding openings within the opposed base members 13 to permit swinging movement of the receptacle 14 about the horizontal axis of the hinge pins 24, as illustrated in FIG. 2.

The bottom portion of the mixing chamber 16 may include a funnel section 25 having a discharge spout 26 with a cap or closure member 27 secured to the mixing chamber 16 by a chain 28 (FIG. 3).

The receptacle 14 may be latched in its upright position by a spring-biased latch pin 30 (FIGS. 1 and 2) adapted to be received in a corresponding opening 31 (FIGS. 1 and 5) in the side wall of the receptacle 14.

Figure 4:
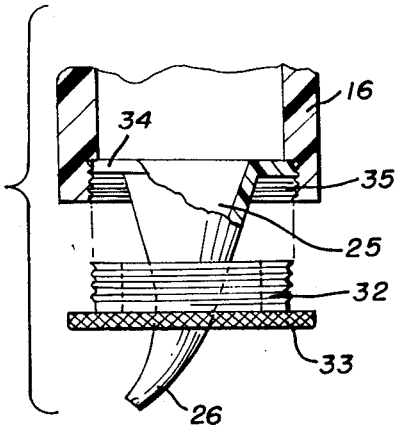
FIG. 4 is an enlarged fragmentary section taken along the line 4—4 of FIG. 3.

As disclosed in FIG. 4, the funnel-shaped section 25 may be a separate piece surrounded by an adapter ring 32 having external threads and a cap 33 for receiving the funnel-shaped section 25. The funnel section 25 preferably has a radially extending annular lip 34 adapted to be sealed in an annular recess 35 within the lower portion of the inside surface of the mixing chamber 16. The recess 35 is internally threaded for threadedly receiving the externally threaded adapter ring 32.

Mounted on the upper end portions of the upright guide rods 12 is an elongated support bracket 36. The support bracket 36 includes an elongated support frame 37 to which may be attached an electric motor 38. The opposite ends of the frame 37 are journaled coaxially to a pair of collars 39 and 40 slidably received upon the opposite guide rods 12 for vertical slidable movement upon the guide rods 12. The left end of the support frame 37, as viewed in FIG. 1, is connected by the hinge pin or journal pin 41 to the collar 39, while the right end of the frame 37 is connected by the hinge pin 42 to the right collar 40.

The support frame 37 is maintained in its level operative position or in various pivotal adjusted positions relative to the collars 39 and 40 by a spring 44 coiled about the hinge pin 42 urging the frame 37 toward the left to cause radial teeth 45 mounted on the left end of the frame 37, and on the inner surface of the collar 39 to interdigitate to prevent rotation of the support bracket 36.

Operatively connected to and depending from the electric motor 38 is an elongated mixer shaft 46. The mixer shaft 46 extends coaxially through a hollow, cylindrical plunger member 48. The mixer shaft 46 is journaled, both for rotary and axial movement within the upper bearing 49 and the lower bearing 50 formed in the respective top and bottom portions of the hollow plunger member 48.

Fixed upon the bottom end of the mixer shaft 46 is a mixer head 52 including a mixer blade, which is located beneath a bottom wall 53 of the plunger member 48.

The hollow plunger member 48 is preferably cylindrical having an outer diameter which is slightly less than the inner diameter of the mixing chamber 16, so that the cylindrical plunger member 48 and the mixer head 52 are free to descend within the interior of the mixing chamber 16. Preferably, the lower portion of the outer cylindrical wall of the plunger member 48 is provided with an annular, flexible sealing ring 54 adapted to snugly engage the inner surface of the mixing chamber 16 in order to seal the space within the mixing chamber 16 below the annular sealing ring 54, as best disclosed in FIG. 5.

The interior of the hollow plunger member 48 is completely closed or confined, except for an upper opening 55 in the top wall and a bottom opening 56 in the bottom wall 53 of the hollow plunger member 48. The openings 55 and 56 receive therethrough a tubular suction conduit or hose 57 connected to a vacuum pump P. The bottom end portion 58 of the suction conduit 57 projects slightly below the bottom wall 53 through an aperture in a shield 66. The discharge opening in the bottom end portion 58 is covered by a screen 67 to prevent ingredients in the mixing chamber 16 from being sucked into the conduit 57.

A plurality of vertically spaced latch notches 59 may be formed in the upright right guide post 12 to receive a spring-loaded latch pin 60, when it is desired to release the support bracket 36 for vertical slidable movement along the guide rods 12 and to hold the support bracket 36 at corresponding elevations. When the latch pin 60 is pulled outward away from the notch 59, the support bracket 36 and motor 38 may be manually depressed against the action of coil springs 61 about the guide posts 12. The springs 61 normally bias the collars 39 and 40, and thus the support bracket 36, to an elevated, inoperative position, such as that disclosed in FIG. 1.

A set screw 79 may be inserted through collar 39 to frictionally engage left guide rod 12 to control vertical movement of support bracket 36 along guide rod 12.

When the support bracket 36 is depressed to urge the hollow cylinder 38 and cutter head 52 into the interior of the mixing chamber 16, the bracket 36 may be locked in the lower position by releasing the latch pin 60 to enter its corresponding latch notch 59. Coil spring 62 (FIG. 8) may be utilized to urge the latch pin 60 inward to its latched position, if desired.

Also, if desired, vertically adjustable stop collars 63 be secured in various vertical positions upon the guide post 12, if desired, by set screw 64.

In the operation of the apparatus 10, dental ingredients to be mixed may be introduced into the mixing chamber 16 by pouring or by any other method, either before or after the mixing chamber 16 is installed within the receptacle 14. As disclosed in FIG. 1, two different dental ingredients are discharged into the mixing chamber 16, supported in the receptacle 14, by charge syringes 23 through the inlet spouts 21.

The upper portion of the side wall of the cylindrical plunger 48 may be provided with a pair of diametrically opposed stop lugs 77 which are in vertical registry with the upward opening slots 78 in the flared mouth 17 of the mixing chamber 16. Thus, the slots 78 provide a lower limit for the descent of the plunger 48 within the mixing chamber 16 when the stop lugs 77 engage the slots 78, if desired.

Figure 5:
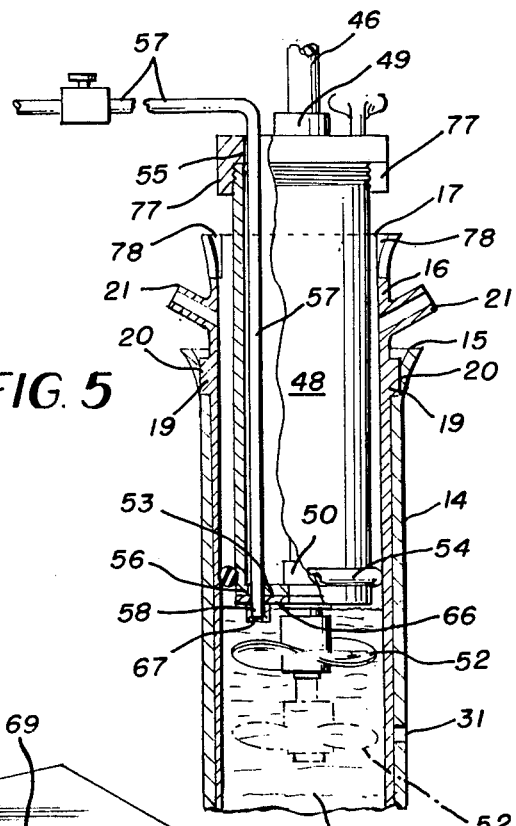
FIG. 5 is an enlarged fragmentary sectional elevation taken through the mixing chamber and its holding receptacle, and illustrating the plunger and mixer head in a lower operative position received within the mixing chamber, and also disclosing in phantom, the mixer head in a lower mixing position.

The latch pin 60 is then withdrawn from its upper latch notch 59 to permit the bracket 36 to be depressed until the plunger member 48 and the cutter head 52 are lowered into an operative position within the mixing chamber 16, such as that position disclosed in FIG. 5. Preferably, the plunger member 48 is lowered until its bottom wall 53 is proximate to or in engagement with the top surface of the dental ingredients 65 received within the mixing chamber 16. The bracket 36 may then be latched in the lower mixing position, as previously described. The annular sealing ring 54 seals the space within the mixing chamber 16 below the sealing ring 54. The vacuum pump P is then actuated to suck air through the suction conduit 57 from the space within the mixing chamber 16 occupied by the material 65. The action of the vacuum pump P reduces the voids and bubbles within the material 65 to provide a more homogeneous mixture.

The electric motor 38 is then driven and energized to drive the mixer shaft 46, which rotates within its bearings 49 and 50 to drive the mixer head 52. If desired, to obtain a better mix, or to mix the ingredients 65 at varying levels within the chamber 16, the support bracket 36 may be released by removing the latch pin 60 and manually depressing the racket 36 and motor 38 to cause the mixer shaft 46 to descend to a lower mixing level, such as illustrated by the phantom position disclosed in FIG. 5.

After the ingredients 65 have been mixed, the motor 38 is de-energized. The latch pin 60 is then unlatched to permit the compressed coil springs 61 to release their energy and thrust the collars 39 and 40 upward. The bracket 36, the mixer shaft 46, the mixer head 52 and the plunger member 48 are then elevated to their inoperative position, such as that disclosed in FIG. 1.

The support bracket 36 may then be rotated about its hinge pins 41 and 42 to a position such as that disclosed in FIG. 2 to provide a clearance or working space above the receptacle 14. A mixing chamber 16 in the receptacle 14 may then be pulled upwardly and removed from the receptacle 14. The mixing chamber 16 may be carried directly to the dental chair where the patient is sitting and the mixed contents may be discharged through the spout 26, after the cap 27 has been removed directly into the cavity of the patient's tooth.

Instead of rotating the bracket 36 about its hinge pins 41 and 42 to the tilted position disclosed in FIG. 2, the receptacle 14 may be rotated about its hinge pins 24 to the phantom position 14' disclosed in FIG. 2 in order to remove the mixing chamber 16 from the receptacle 14.

Figure 7:
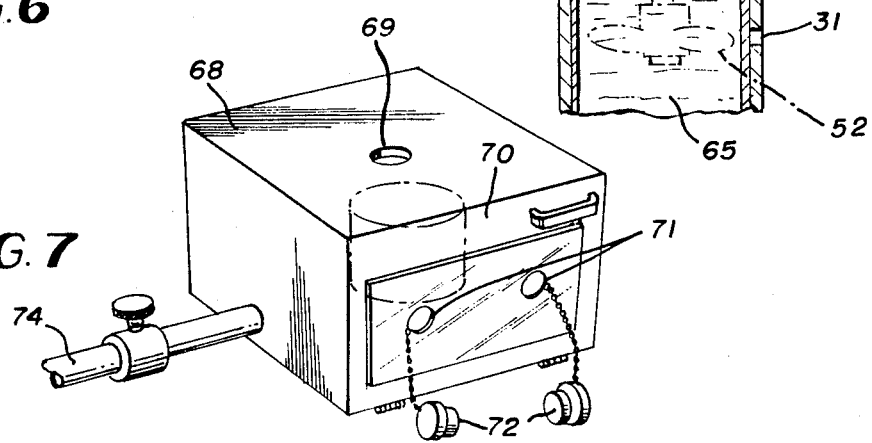
FIG. 7 is a top perspective view of the hollow discharge chamber illustrated in FIG. 1 connected to a suction pipe shown fragmentarily.

Another option for discharging the contents is to position a receptacle or box, such as the receptacle 68 (FIGS. 1 and 7) beneath the receptacle 14. The box 68 has an inlet hole 69 in the top thereof for receiving the mixed ingredients 65 from the discharge spout 25 in the bottom of the mixing chamber 16. Preferably, the box 68 is completely enclosed except for the inlet opening 69 and for a hinged trap door 70 including a pair of finger holes 71, both of which may be closed by corresponding caps 72, when not in use, and for a vacuum pipe 74. After the contents of the mixing chamber 16 are discharged through the inlet hole 69 into the interior of the box 68, a vacuum is created through the vacuum conduit 74 by virtue of a vacuum pump, not shown. The dentist or dental assistant may insert his or her fingers through the finger holes 71, or may open the hinged trap door 70 to insert their hands into the box 68 to manipulate the mixed ingredients, such as in a molding operation, in order to mold a false tooth.

After the mixing procedure, if it is desired to discharge the mixed contents 65 through the bottom of the mixing chamber 16, while the mixing chamber 16 is received in the receptacle 14, the cap 27 is removed and the bracket 36 is further depressed against the action of the spring 60 to utilize the plunger member 48 to force the contents of the mixing chamber 16 downward through the funnel section 25, and out through the discharge pipe 26 into a receptacle, such as the box 68.

If, after the mixing process, the plunger member 48 and mixer head 52 are removed from the mixing chamber and the mixing chamber 16 is removed from the receptacle 14 for transport to another work station, a manual plunger member 75 (FIG. 6) may be utilized to force the ingredients in the separated mixing chamber 16 through the discharge spout 26. Thus, for example, if the mixing chamber 16 filled with the for discharge of the contents directly into the tooth cavity, the plunger member 75 may be inserted into the top open end 17 of the mixing chamber 16 and urged downwardly to assist in discharging the mixed contents through the open spout 26 directly into the cavity.

It will therefore be seen that a dental mixing and dispensing apparatus 10 has been provided which may be operated by a single operator, either the dentist or his assistant, and may be operated quickly for rapidly mixing and discharging the contents. Moreover, the apparatus 10 may be utilized in several optional ways in order to either discharge the contents at the site of the apparatus 10, or to remove, transport, and discharge the contents at a site remote from the site of the apparatus 10.

Furthermore, not only are the dental ingredients actively and thoroughly mixed by the apparatus, but the mixed ingredients are devoid of most of the air and bubbles normally found in a dental mixture.

It is also within the scope of this invention to utilize a mixing chamber 16 made of materials which may be readily and economically disposed of after the mixing chamber has been used, and replaced by a like mixing chamber 16.

What is claimed is:

1. An apparatus for mixing dental impression materials, comprising:
   (a) a base,
   (b) a mixing chamber having an upright longitudinal axis, an upper open end, a bottom end portion, and a substantially uniform cross-section, adapted to receive dental impression materials,
   (c) means holding said mixing chamber on said base in a substantially upright position,
   (d) an elongated plunger member having a longitudinal axis and a substantially uniform cross-section less than the cross-section of said mixing chamber,
   (e) an elongated mixer shaft longer than said plunger member and extending coaxially through said plunger member and having upper and lower end portions, (f) a mixer head on said lower end portion below said plunger member, (g) support means on said base supporting said mixer shaft and said plunger member for vertical reciprocal movement coaxially of said mixing chamber between a lower operative position in which said plunger member is telescopingly received in said mixing chamber, and an elevated inoperative position in which said mixer shaft and plunger member are above said mixing chamber, (h) bearing means supporting said mixer shaft in said plunger member for relative coaxial movement to permit said mixer head to descend from said operative position to a mixing position within said mixing chamber, (i) a suction conduit for removing air from said mixing chamber while said plunger member is in said operative position, and (j) drive means for driving said mixer shaft to rotate said mixer head.

2. The invention according to claim 1 further comprising seal means between said plunger member and said mixing chamber in said operative position to permit the passage of air from said mixing chamber only through said suction conduit.

3. The invention according to claim 1 in which said support means comprising an elongated guide rod projecting vertically upward from said base substantially above said mixing chamber, a support bracket mounted on said guide rod for vertical reciprocable movement, and means supporting the upper end portion of said mixer shaft in said support bracket for rotary movement, and spring means normally biasing said support bracket to said raised inoperative position.

4. The invention according to claim 3 further comprising latch means for locking said support bracket on said guide rod in said lower operative position.

5. The invention according to claim 3 in which said drive means comprises a motor mounted on said support bracket in operative driving engagement with said mixer shaft.

6. The invention according to claim 3 further comprising stop means on said mixer shaft cooperating with said bearing means to limit the axial movement of said plunger member on said mixer shaft to a lower position immediately above said mixer head and to an upper position below said support bracket.

7. The invention according to claim 3 in which said mean connecting said support bracket to said guide rod comprises journal means to permit swinging movement of said mixer shaft and plunger member to a position away from said longitudinal upright axis of said mixing chamber.

8. The invention according to claim 3 in which said means holding said mixing chamber comprises a normally upright receptacle with a slightly larger cross-section than said mixing chamber for receiving said mixing chamber, journal means supporting said receptacle in said base for swinging movement of said receptacle about a horizontal axis, and latch means for holding said receptacle in an upright operative position to permit said mixing chamber to receive said plunger member in said operative position.

9. The invention according to claim 8 in which said upper open end of said mixing chamber projects above the upper end of said receptacle, and inlet openings formed in the upper end portion of said mixing chamber above said receptacle for receiving dental impression materials.

10. The invention according to claim 9 in which said inlet openings comprise tubular inlets, each tubular inlet being adapted to receive the discharge spout of a syringe containing said dental impression materials for discharge of said impression materials from said syringe through said tubular inlet into said mixing chamber.

11. The invention according to claim 1 further comprising a discharge opening in said bottom end portion of said mixing chamber.

12. The invention according to claim 11 in which said discharge opening comprises a discharge spout in said bottom portion of said mixing chamber having a bottom aperture, and means for closing said bottom aperture.

13. The invention according to claim 11 further comprising a hollow discharge receptacle for insertion below said discharge opening for receiving mixed dental impression materials from said discharge opening into said hollow discharge receptacle, and means for evacuating said receptacle, an access opening to the interior of said hollow discharge chamber for manipulating the materials within said chamber, and closure means for said access opening.

* * * * *